United States Patent [19]

Henne et al.

[11] Patent Number: 4,673,506

[45] Date of Patent: Jun. 16, 1987

[54] CLEANING TREATMENT FOR BLOOD COMPARTMENTS OF DIALYZATORS

[75] Inventors: Werner Henne; Michael Pelger, Wuppertal, both of Fed. Rep. of Germany

[73] Assignee: AKZO NV, BM Arnhem, Netherlands

[21] Appl. No.: 801,520

[22] Filed: Nov. 25, 1985

Related U.S. Application Data

[63] Continuation of Ser. No. 615,474, May 29, 1984, abandoned.

[30] Foreign Application Priority Data

May 28, 1983 [DE] Fed. Rep. of Germany ....... 3319504

[51] Int. Cl.⁴ .............................................. B01D 13/04
[52] U.S. Cl. ...................................... 210/636; 134/26; 210/321.3; 422/22; 422/26; 422/34
[58] Field of Search ................... 134/26; 210/636, 646, 210/321.3; 422/22, 26, 27, 34, 44, 48

[56] References Cited

U.S. PATENT DOCUMENTS

| | | | |
|---|---|---|---|
| 3,871,913 | 3/1975 | Shaldon | 210/636 |
| 4,166,031 | 8/1979 | Hardy | 210/636 |
| 4,176,070 | 11/1979 | Sakurada et al. | 422/24 |
| 4,176,156 | 11/1979 | Asanuma et al. | 422/26 |
| 4,411,866 | 10/1983 | Kanno | 422/26 |
| 4,588,407 | 5/1986 | Isono et al. | 210/646 |

FOREIGN PATENT DOCUMENTS

| | | | |
|---|---|---|---|
| 55-116354 | 9/1980 | Japan | 422/22 |
| 59-22558 | 2/1984 | Japan | 422/22 |

*Primary Examiner*—Peter Hruskoci
*Attorney, Agent, or Firm*—Michael J. Striker

[57] ABSTRACT

A cleaning treatment is disclosed for the blood compartments of dialyzators which is effected still in the preparation stage. The dialyzators contain membranes of cellulose in the form of hollow filaments, tubes or flat foils. The cleaning treatment embraces the following measures:

washing with water or aqueous solutions and evacuation of the compartments, then filling with a mixture of water, glycerin and alcohol and drying after a renewed evacuation—or, filling with water or aqueous solutions and subsequently closing the entrance and exit of the blood compartment. As a third measure, the compartments are sterilized with gamma radiation and/or ethylene oxide and/or superheated steam.

22 Claims, 2 Drawing Figures

CLEANING TREATMENT FOR BLOOD COMPARTMENTS OF DIALYZATORS

This application is a continuation of application Ser. No. 15,474, filed May 29, 1984 now abandoned.

BACKGROUND OF THE INVENTION

In the field of hemodialysis, hollow filament dialyzators specifically of cellulose have succeeded worldwide in contrast to those of so-called flat and tube membranes, since they clearly possess a series of advantages, not only with regard to their space-saving construction, high efficiency and easy manipulability, but also insofar their behavior to human blood by means of well regulated flow distribution.

Cellulocic hollow filaments such as e.g., those which have been prepared according to the cuoxam or cupramonium technique are afflicted, however, with the disadvantage that their interior side (=subsequent blood side) is not exposed during the manufacturing process to the equally intensive washing procedure but can be washed practically only from the outer side. This factor leads to a difference in the residual content of extractable yet unknown substances in a molecular weight range between about 1000 and 100,000.

Conjectures have though been expressed that this is possibly responsible for incidentally occurring anaphylactic or other incompatibility reactions upon dialysis patients either alone or in connection with ethylene oxide, i.e., a sterilization means.

SUMMARY OF THE INVENTION

It is therefore an object according to the present invention to provide a method for the cleaning of hollow filament dialyzators during the preparation stage of the dialyzators and which avoids the disadvantages of the missing water washing of the hollow filament interior side and provides a possibility of effecting in case needed the sterilization without ethylene oxide.

The hollow filament interior is filled with a filling liquid from the production stages.

Previously known techniques for this include the production of water-filled hollow filament dialyzators in connection with an addition of formalin or in connection with hot vapor sterilization or so-called gamma iradiation-sterilization. In all cases it is perceived by the manufacturer of the dialyzator to be very troublesome and uneconomical that with every dialyzator a high liquid weight of several additional hundred grams has to be evacuated, whereas the hospitals, laboratories, and clinics, (i.e., the consumers for the dialyzators) object to the poor handleability and the long time requirements for the washing out before the start-up sequence.

In spite of the above set forth disadvantages, dialyzators delivered "dry" are clearly preferred by the users; nonetheless, there has been no success in providing e.g., dry, alpha-irradiated dialyzators, since the irradiation lowers the hydraulic permeability of cellulose hollow filaments to an extent of about 40%. Water washing and subsequent drying has, on the other hand, not been successful with already prepared dialyzators since the hollow filaments crimp so strongly upon the drying (i.e., about 8%) that the resulting force of contraction leads either to a destruction of the heads, a retraction of the embedding layer or a dissolving out of individual filaments and thus to localized difficulties such as e.g., perviousness.

Two different manners have been discovered for attainment of the object according to the present invention as set forth above and which are identical in their first stage:

1. The prepared dialyzators are washed essentially with water or an aqueous electrolyte solution or an aqueous solvent mixture of an organic nature (i.e., the washing solution) by means of a closed circulation at the blood side (the so-called blood compartment) within a period of approximately 5 to 15 minutes. The liquid is allowed to run off and the blood compartment of the dialyzator is subsequently filled with a mixture of water + glycerin + alcohol (i.e., a ternary solution), a short period after which it is emptied out and dried in a warm airstream at temperatures of about 50° C. Therewith is established the glycerin content of the mixture from 25% by weight, surprisingly; and, moreover, that the filaments do not shrink upon drying and also that the ultrafiltration rate does not decrease, whereas it otherwise always was approximately 40% upon the drying of a wet filament.

The dry hollow filament dialyzator can then be sterilized with ethylene oxide or gamma irradiation.

2. The prepared dialyzator is washed essentially as set forth under 1. supra on the blood side with water or one of the mentioned aqueous solutions. The liquid is allowed to run off and then the blood compartment-deviating from 1. supra-is filled only with fresher washing solution after which the inlet and outlet of the blood compartment are closed tightly. An gamma irradiation and/or an equivalent sterilization is then performed. It has surprisingly been determined that also in this case the ultrafiltration rate of the dialyzator is maintained.

The dialyzators treated according to the present invention can in this state be immediately delivered, insofar as an ethylene oxide treatment is not undertaken. (In the case of an ethylene oxide sterilization, customarily requiring a quarantine period of about 4 weeks is necessary for out-gassing.)

Figure 1:
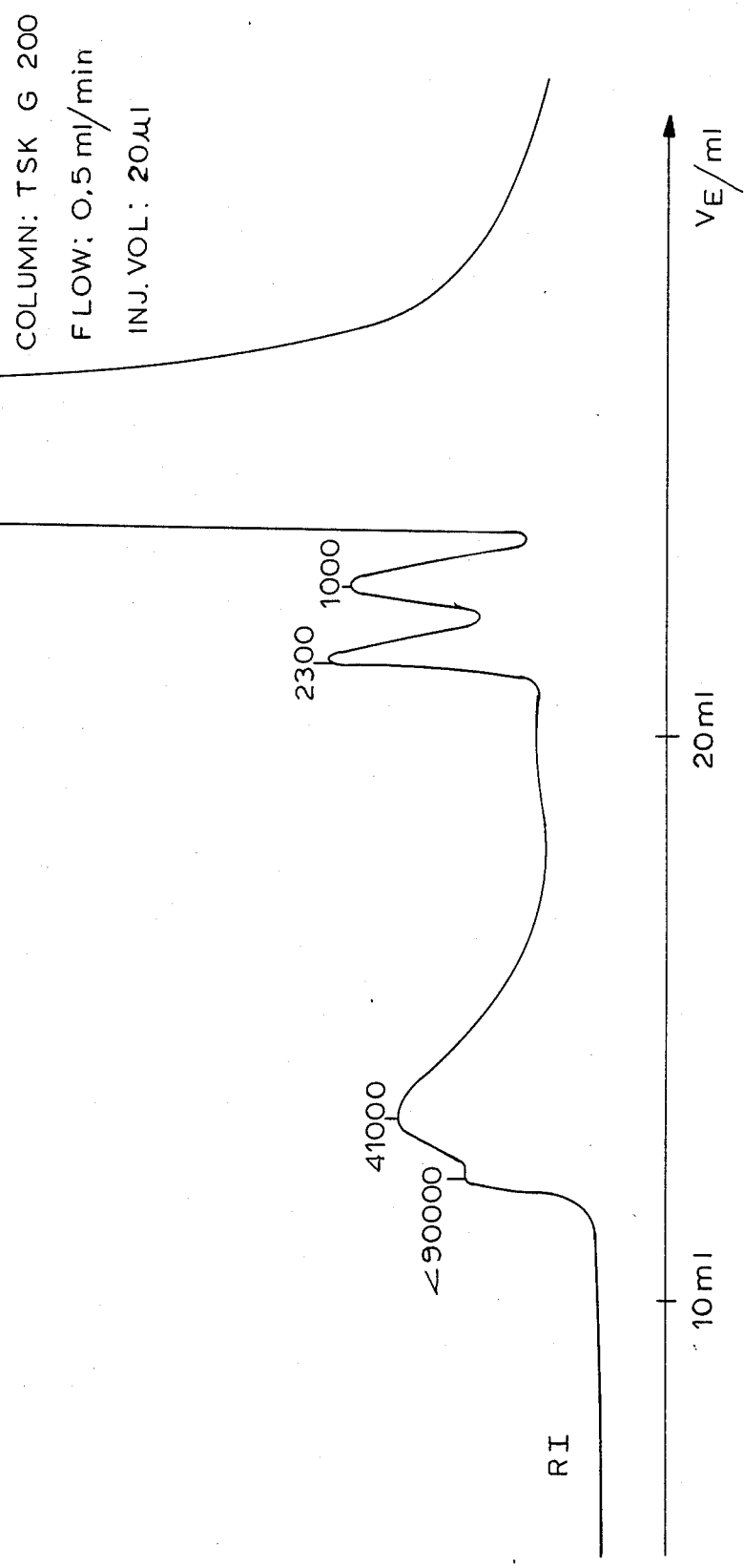
FIG. 1 is a high pressure fluid chromatogram of an extract sample recovered from the blood side of a typical commercially available hollow filament dialyzator.

The chromatogram (FIG. 1) of extracts obtains at the blood side of hollow filament dialyzators as are customarily employed in commerce is indifferent as to whether or not these have been cleaned during the preparation process with hydrophobic solvents of the freon type (trichlorotrifluoroethane 113), with alcohols, such as ethanol, methanol, isopropanol or mixtures thereof. The graph shows peaks for substances in the ranges 90,000, 40,000, 2,200 and 1,000. These molecular weights are coordinated to the substances after a standarization with pullulane.

Figure 2:
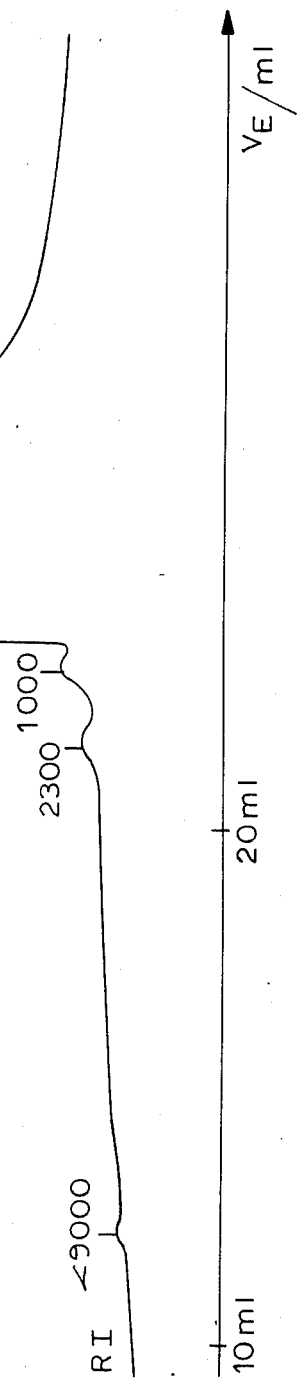
FIG. 2 is a high pressure fluid chromatogram of an extract sample recovered from a dialyzator treated according to the present invention.

When dialyzators are subjected at the end of the dialyzator preparation process to the techniques set forth under 1. or 2. supra, and later the blood side is extracted (to the interior side) with water, the extract in this case is practically free of the peaks, as shown in FIG. 2.

The graph of FIG. 2 is valid also for a cellulose hollow filament dialyzator with which surrender of the full extractable portion is effected in the clinic, in which case however, it has been rinsed in the clinic an unusually long period of time with water and essentially end-cleaned in a single pass by means of the throughput of water. Accordingly, it is a great advantage if the dialyzators already leave the preparation process with the mentioned freeness from substances extractable by means of water.

A further and previously known effect has been discovered during the testing: if in the ternary solution the glycerin content rises above 50% by weight with equal or different distribution of the balance under both other components, alcohol and water, then the ultrafiltration rate of the dialyzator increases even further compared to the starting value. One can thus despite subsequent drying or gamma-sterilization increase the ultrafiltration rate of the dialyzator according to the extent of the addition of glycerin, and therewith the method according to the present invention is of advantageous utility in an additional sense.

EXAMPLE 1

A cellulose hollow filament dialyzator of the type CF1211 from the firm Baxter Travenol, Inc., is rinsed for a period of 15 minutes at the blood side and in circulation with a flow of 200 ml/min. of purest water at room temperature. The total volume of the water amounts to 2 l. After running off the water the dialyzator is filled at the blood side at room temperature with a solution of fifty percent isopropanol
twenty-five percent glycerin
twenty-five percent water.

After a period of 5 minutes, the dialyzator is drained and then dried in a vacuum for 3 hours at 50° C. The dialyzator remains leakproof, the filaments themselves remaining individual and not stuck together, while the embedding layer at the head side remains unimpaired.

Thereafter, the ultrafiltration rate is tested with water and amounts to 4.3 ml/h.m$^2$.mm Hg which corresponds to the starting value of the employed filament type (e.g., cellulose hollow filament manufactured according to the cupramonium technique). An apprehended 40% decrease is avoided.

A second dialyzator from the same lot, which has been rinsed with water in similar manner, is then, however, instead of the above solution, filled only with water and in similar manner, after-treated as set forth above, does not stand the drying. The PU-embedding layer is drawn inward 2 cm and is permeable whereby no measurement of the ultrafiltration rate is any longer possible.

The method according to the present invention is suitable moreover, for the treatment of flat membrane and tube membrane dialyzators, whereby the increased ultrafiltration rate takes on particular significance.

EXAMPLE 2

2 hollow fiber dialyzers of GAMBRO, type GF-80-H, fitted with cellulosic hollow fibres produced by the cuprammonium process, having a wall thickness of 8 μm and an inside diameter of 200 μm, type "Cuprophan ®F1", were rinsed for 15 minutes with pyrogen-free water of room temperature being circulated in the blood compartment at a flow rate of 200 ml/min, the volume of water being 2 l.

Then the rinsing water was drained out and the dialyzers were primed with fresh water and rinsed in a single pass with 0.5 l. The blood inlet and blood outlet were then hermetically sealed with plastic caps. One of these dialyzers with a filled blood compartment was exposed to a radiation dose of 2.7 Megarad in a γ-ray unit; the other dialyzer was left untreated.

Subsequently, these dialyzers were subjected to a permeability test giving the following results:

|  | Dialyzer exposed to γ-rays | Unexposed dialyzer |
| --- | --- | --- |
| Ultrafiltration rate ml/h m$^2$ mm Hg | 4.53 | 4.55 |
| Clearance for creatinine ml/min | 137 | 136 |

The permeability data are to be considered identical within the tolerance limits. They also correspond to the values of dialyzers sterilized with ethylene oxide.

We claim:

1. A method for the cleaning of blood compartments of dialyzators during the preparation stage with means for washing, said dialyzators containing membranes of cellulose in hollow filament, tube or flat form, comprising:

washing said blood compartments with pure water or water containing at least one electrolyte and organic solvent;

allowing the pure water or water containing at least one electrolyte and organic solvent, used to wash said blood compartments, to run off;

filling said blood compartments with a mixture of water, glycerin and alcohol;

allowing said mixture to run off;

drying said blood compartments; and sterilizing said blood compartments.

2. The method according to claim 1, wherein said washing step is carried out with water for a period of between 5-15 minutes.

3. The method according to claim 2, wherein said washing is carried out for a period of 15 minutes.

4. The method according to claim 1, wherein said drying step of said blood compartments is carried out at approximately 50° C.

5. The method according to claim 1, wherein said sterilizing step of said blood compartment occurs by means selected from the group consisting of gamma-irradiation, ethylene oxide and hot vapor, and, further comprising said cellulose membranes being prepared from cellulose cuoxam solution.

6. A method for cleaning blood compartments of dialyzators during the preparation stage with means for washing, said dialyzators containing membranes of cellulose in hollow filament, tube or flat form, comprising:

washing said blood compartments with pure water or water containing at least one electrolyte and organic solvent;

allowing the pure water or water containing at least one electrolyte and organic solvent, used to wash said blood compartments, to run off;

filling said blood compartments with a mixing of water, glycerin and alcohol containing at least 25% by weight glycerin;

allowing said mixture to run off;

drying said blood compartments; and sterilizing said blood compartments.

7. The method according to claim 6, wherein said washing step is carried out with water for a period of 5-15 minutes.

8. The method according to claim 7, wherein said washing occurs for a period of 15 minutes.

9. The method according to claim 6, wherein the alcohol in said mixture of water, glycerin and alcohol is isopropanol.

10. The method according to claim 6, wherein said mixture of water, glycerin and alcohol contains approximately 25% water, 25% glycerin and 50% isopropanol.

11. The method according to claim 10, wherein said mixture fills said blood compartments for 5 minutes.

12. The method according to claim 6, wherein said drying step of said blood compartments is carried out at approximately 50° C.

13. The method according to claim 6, wherein said sterilizing step of said blood compartment occurs by means selected from the group consisting of gamma-irradiation, ethylene oxide and hot vapor, and, further comprising said cellulose membranes being prepared from cellulose cuoxam solution.

14. A method for cleaning blood compartment of dialyzators during the preparation stage with water, said dialyzators containing membranes of cellulose in hollow filament, tube or flat form, comprising:
   washing said blood compartments with water for 5-15 minutes;
   allowing the water to run off;
   filling said blood compartments with a mixture of approximately 25% water, 25% glycerin and 50% isopropanol;
   allowing said mixture to run off;
   drying said blood compartments; and
   sterilizing said blood compartments.

15. The method according to claim 14, wherein said washing step is carried out with water for a period of 15 minutes.

16. The method according to claim 14, wherein said mixture fills said blood compartments for 5 minutes.

17. The method according to claim 14, wherein said drying step of said blood compartments is carried out at approximately 50° C.

18. The method according to claim 14, wherein said washing step of said blood compartments is carried out with water for 15 minutes, after which the water is allowed to run off, said filling step of said blood compartments is carried out with said mixture for 5 minutes, after which said mixture is allowed to run off, and said drying step of said blood compartments occurs at 50° C.

19. The method according to claim 14, wherein said sterilizing step of said blood compartments occurs by means selected from the group consisting of gamma-irradiation, ethylene oxide and hot vapor, and, further comprising said cellulose membranes being prepared from cellulose cuoxam solution.

20. A method for cleaning blood compartments of dialyzators during the preparation stage with water, said dialyzators containing membranes of cellulose in hollow filament, tube or flat form, comprising:
   washing said blood compartments with water for 5-15 minutes;
   filling said blood compartments with a mixture of approximately 25% water, 25% glycerin and 50% isopropanol for 5 minutes;
   allowing said mixture to run off;
   drying said blood compartments; and
   dry sterilizing blood compartments by means selected from the group consisting of gamma-irradiation, ethylene oxide and hot vapor.

21. The method according to claim 20, wherein said washing step is carried out with water for a period of 15 minutes.

22. The method according to claim 20, wherein said drying step of said blood compartment is carried out at approximately 50° C.

* * * * *